(12) United States Patent
Griffey et al.

(10) Patent No.: US 6,441,150 B1
(45) Date of Patent: Aug. 27, 2002

(54) COMPOUNDS FOR THE SYNTHESIS OF NUCLEOTIDE OR OLIGONUCLEOTIDE PHOSPHORAMIDITES

(75) Inventors: Richard H. Griffey, Vista; Douglas L. Cole, San Diego; Vasulinga Ravikumar, Carlsbad, all of CA (US)

(73) Assignee: ISIS Pharmaceuticals, Inc., Carlsbad, CA (US)

( * ) Notice: Subject to any disclaimer, the term of this patent is extended or adjusted under 35 U.S.C. 154(b) by 0 days.

(21) Appl. No.: 09/331,837

(22) PCT Filed: Dec. 16, 1997

(86) PCT No.: PCT/US97/23269

§ 371 (c)(1),
(2), (4) Date: Aug. 23, 1999

(87) PCT Pub. No.: WO98/29429

PCT Pub. Date: Jul. 9, 1998

(51) Int. Cl.[7] .................. C07H 21/00; C07H 21/02; C07H 21/04
(52) U.S. Cl. ................. 536/23.1; 536/25.31; 536/25.34
(58) Field of Search ............................. 536/23.1, 25.34, 536/25.31

(56) References Cited

U.S. PATENT DOCUMENTS

| | | | | |
|---|---|---|---|---|
| 3,687,808 A | * | 8/1972 | Merigan, Jr. et al. | |
| 4,415,732 A | * | 11/1983 | Caruthers et al. | |
| 4,458,066 A | * | 7/1984 | Caruthers et al. | |
| 4,500,707 A | * | 2/1985 | Caruthers et al. | |
| 4,668,777 A | * | 5/1987 | Caruthers et al. | |
| 4,959,463 A | * | 9/1990 | Froehler et al. | 536/23.1 |
| 5,212,295 A | * | 5/1993 | Cook | 536/26.7 |
| 5,264,566 A | * | 11/1993 | Froehler et al. | 536/25.34 |
| 5,268,464 A | * | 12/1993 | Brill | 536/25.3 |
| 5,489,677 A | * | 2/1996 | Sanghvi et al. | 536/22.1 |
| 5,548,076 A | * | 8/1996 | Froehler et al. | 536/25.34 |
| 5,591,584 A | * | 1/1997 | Chang et al. | 435/6 |
| 5,623,070 A | * | 4/1997 | Cook et al. | 536/27.6 |
| 5,792,844 A | * | 8/1998 | Sanghvi et al. | 536/23.1 |
| 5,955,600 A | * | 9/1999 | Griffey et al. | 536/25.34 |
| 6,103,891 A | * | 8/2000 | Griffey et al. | 536/25.34 |
| 6,166,197 A | * | 12/2000 | Cook et al. | 536/24.5 |

OTHER PUBLICATIONS

Ven'yaminova et al.(I), "Phosphorylation of Oligonucleotides by β–Cyanoethylphosphite," *Bioorg Khim.(Russian)*, 15(6), 844,846 (1989); *Chem. Abstracts*, 112, Abstract No. 56531 (1990); only abstract supplied.*

Ven'yaminova et al.(II), "Automated H–Phosphonate Synthesis of Oligoribonucleotides Using 2'-O–Tetrahydropyranyl Protecting Group," *Bioorg. Khim.(Russian)*, 16(7), 941–950 (1990; *Chem. Abstracts*, 113, Abstract No. 231905 (1990; only abstract supplied.*

Brill (II), "Facile Methods to Recycle Nucleosides During Solid Phase Synthesis of Oligonucleotides," *Tetrahedron Letters*, 35(19), 3041–3044 (May 9, 1994).*

Brill (III), Thioalkylation of Nucleoside–H–Phosphonates and Its Application to Solid Phase Synthesis of Oligonucleotides, *Tetrahedron Letters*, 36(5), 703–706 (Jan. 30, 1995).*

Gryaznov et al., "A New Method for the Synthesis of Oligodeoxyribonucleotides Containing Internucleotide Phosphoramidate Bonds," *Tetrahedron Letters*, 31(22), 3205–3208 (1990).*

Wada et al., "2–Cyanoethyl Nucleoside 3'-Phosphonates as Novel Starting Materials for Oligonucleotide Synthesis," *Tetrahedron Letters*, 29(33), 4143–4146 (1988).*

Jankowska et al., "Studies on Aryl H–Phosphonates. I. An Efficient Method for the Preparation of Deoxyribo– and Ribonucleoside 3'-H–Phosphonate Monoesters by Transesterification of Diphenyl H–Phosphonate Monoesters by Transesterification of Diphenyl H–Phosphonate," *Tetrahedron Letters*, 35(20), 3355–3358 (May 16, 1994).*

Beaucage et al., "Advances in the Synthesis of Oligonucleotides by the Phosphoramidite Approach", *Tetra.*, 1992, 48(12), 2223–2311.

Cook, "Medicinal chemistry of antisense oligonucleotides—future opportunities", *Anti–Cancer Drug Design*, 1991, 6, 585–607.

Cook, *Medicinal Chemistry Strategies for Antisense Research, in Antisense Research and Applications.*, Crooke et al. (eds.), 1993, CRC Press, Inc. Boca Raton, FL.

Delgardo et al., "The Uses and Properties of PEG–Linked Proteins", *Critical Rev. in Therapeutic Drug Carrier Systems*, 1992, 9(3,4), 249–304.

De Memaeker et al., "Amides as Substitute for the Phosphodiester Linkage in Antisense Oligonucleotides", *Synlett.*, 1993, 10, 733–736 (Oct., 1993).

De Mesmaeker et al., "Comparison of Rigid and Flexible Backbones in Antisense Oligonucleotides", *Bioorg. Medic. Chem. Lett.*, 1994, 4(3), 395–398.

De Mesmaeker et al., "Replacement of the Phosphodiester Linkage in Oligonucleotides: Comparison of Two Structural Amide Isomers", *Bioorg. Medic. Chem. Lett.*, 1994, 4(7), 873–878.

Englisch et al., "Chemically Modified Oligonucleotides as Probes and Inhibitors", Angew. Chem. Int. Ed. Engl., 1991, 30(6), 613–629 (Jun., 1991).

Hotoda et al., "Tris(2,4,6–Tribromophenoxy) Dichlorophosphorane: A Novel Condensing Agent for Rapid Internucleotidic Bond Formation in the Phosphotriester Approach", *Tetra. Lett.*, 1987, 28(15), 1681–1684.

(List continued on next page.)

OTHER PUBLICATIONS

Primary Examiner—Gary Geist
Assistant Examiner—L. E. Crane
(74) Attorney, Agent, or Firm—Woodcock Washburn Kurtz Mackiewicz & Norris LLP

(57) ABSTRACT

This invention presents novel methods for recovery of phosphoramidites from the waste products of oligonucleotide synthesis. The methods include reacting a tribromophenoxydichlorophosphorane with an H-phosphonate in the presence of an amine.

24 Claims, No Drawings

OTHER PUBLICATIONS

Lebreton et al., "Synthesis of Thymidine Dimer Derivatives Kroschwitz, J.I. (ed.), *Concise Encyclopedia of Polymer Science and Engineering*, John Wiley & Sons, 1990, 858–859. Containing an Amide Linkage and their Incorporation into Oligodeoxyribonucleotides", *Tetra. Lett.*, 1993, 34(40), 6383–6386.

Lebreton et al., "Comparison of two Amides as Backbone Replacement of the Phosphodiester Linkage in Oligodeoxynucleotides", *Tetra. Lett.*, 1994, 35(29), 5225–5228.

Lebreton et al., "Antisense Oligonucleotides with Alternating Phosphodiester–"Amide–3"Linkages", *Synlett.*, 1994, 2, 137–140 (Feb., 1994).

Ouchi et al., "Synthesis and Antitumor Activity of Poly(Ethylene Glycol)s Linked to 5–Fluorouracil Via a Urethane or Urea Bond", *Drug Design and Discovery*, 1992, 9, 93–105.

Ravasio et al., "Selective Hydrogenations Promoted by Copper Catalysis. 1. Chemoselectivity, Regioselectivity, and Stereoselectivity in the Hydrogenation of 3–Substituted Steroids", *J. Org. Chem.*, 1991, 56, 4329–4333.

Secrist et al., Abstract 21, Program and Abstracts, Tenth International Roundtable, Nucleosides, Nucleotides and their Biological Applications, Park City, Utah, Sep. 16–20, 1992.

Sanghvi, Y.S., "Heterocyclic Base Modification in Nucleic acids and their Applications in Antisense Oligonucleotides", *Antisense Research and Applications*, 1993, Chapter 15, CRC Press, Boca Raton, 273–288.

Scremin et al., "Stepwise Regeneration and Recovery of Deoxyribonucleoside Phosphoramidite Monomers during Solid–Phase Oligonucleotide Synthesis", *J. Org. Chem.*, 1994, 59, 1963–1966.

Uhlmann et al., "Antisense Oligonucleotides: A New Therapeutic Principle", *Chem. Rev.*, 1990, 90(4), 543–584 (Jun., 1990).

Wada et al., "Nonoxidative Chlorination of Dialkyl Phosphonates to Dialkyl Phosphorochloridites. A New Approach to Oligonucleotide Synthesis", *J. Org. Chem.*, 1991, 56, 1243–1250.

Wada et al., "Nucleoside 3'–N,N–Dialkylphosphonamidates as Novel Nucleotide Units for the Solution–Phase Oligonucleotide Synthesis", *Tetrahedron*, 1993, 49(10), 2043–2054.

Waldner et al., "Ureas as Backbone Replacements for the Phosphodiester Linkage in Oligonucletodies", *Synlett.*, 1994, 1, 57–61 (Jan., 1994).

Waldner et al., "Synthesis of Oligodeoxyribonucleotides containing Dimers with Carbamate Moieties as Replacement of the Natural Phosphodiester Linkage", *Bioorg. Medic. Chem. Lett.*, 1994, 4(3), 405–408.

Wolfgang, "Facile Methods to Recycle Nucleosides during Solid Phase Synthesis of Oligonucleotides", *Tetra. Lett.*, 1994, 35(19), 3041–3044.

* cited by examiner

COMPOUNDS FOR THE SYNTHESIS OF NUCLEOTIDE OR OLIGONUCLEOTIDE PHOSPHORAMIDITES

FIELD OF THE INVENTION

This invention is directed to novel methods for the preparation of phosphoramidites and oligophosphoramidites. The methods are useful, inter alia, for the preparation of phosphoramidites which are useful, in turn, in the synthesis of oligonucleotide diagnostic reagents, research reagents and therapeutics agents.

BACKGROUND OF THE INVENTION

It is well known that most of the bodily states in mammals, including most disease states, are affected by proteins. Such proteins, either acting directly or through their enzymatic functions, contribute in major proportion to many diseases in animals and man. Classical therapeutics has generally focused on interactions with such proteins in efforts to moderate their disease causing or disease potentiating functions. Recently, however, attempts have been made to moderate the actual production of such proteins by interactions with molecules that direct their synthesis, such as intracellular RNA. By interfering with the production of proteins, it has been hoped to affect therapeutic results with maximum effect and minimal side effects. It is the general object of such therapeutic approaches to interfere with or otherwise modulate gene expression leading to undesired protein formation.

One method for inhibiting specific gene expression is the use of oligonucleotides and oligonucleotide analogs as "antisense" agents. The oligonucleotides or oligonucleotide analogs complimentary to a specific, target, messenger RNA (mRNA) sequence are used. Antisense methodology is often directed to the complementary hybridization of relatively short oligonucleotides and oligonucleotide analogs to single-stranded mRNA or single-stranded DNA such that the normal, essential functions of these intracellular nucleic acids are disrupted. Hybridization is the sequence specific hydrogen bonding of oligonucleotides or oligonucleotide analogs to Watson-Crick base pairs of RNA or single-stranded DNA. Such base pairs are said to be complementary to one another.

Prior attempts at antisense therapy have provided oligonucleotides or oligonucleotide analogs that are designed to bind in a specific fashion to a specific mRNA by hybridization (i.e., oligonucleotides that are specifically hybridizable with a target mRNA). Such oligonucleotides and oligonucleotide analogs are intended to inhibit the activity of the selected mRNA by any of a number of mechanisms, i.e., to interfere with translation reactions by which proteins coded by the mRNA are produced. The inhibition of the formation of the specific proteins that are coded for by the mRNA sequences interfered with have been hoped to lead to therapeutic benefits; however there are still problems to be solved. See generally, Cook, P. D. *Anti-Cancer Drug Design* 1991, 6,585; Cook, P. D. *Medicinal Chemistry Strategies for Antisense Research, in Antisense Research & Applications*, Crooke, et al., CRC Press, Inc.; Boca Raton, Fla., 1993; Uhlmann, et al., *A. Chem. Rev.* 1990, 90, 543.

Oligonucleotides and oligonucleotide analogs are now accepted as therapeutic agents holding great promise for therapeutics and diagnostics methods. But applications of oligonucleotides and oligonucleotide analogs as antisense agents for therapeutic purposes, diagnostic purposes, and research reagents often require that the oligonucleotides or oligonucleotide analogs be synthesized in large quantities, be transported across cell membranes or taken up by cells, appropriately hybridize to targeted RNA or DNA, and subsequently terminate or disrupt nucleic acid function. These critical functions depend on the initial stability of oligonucleotides and oligonucleotide analogs toward nuclease degradation.

A serious deficiency of unmodified oligonucleotides for these purposes, particularly antisense therapeutics, is the enzymatic degradation of the administered oligonucleotides by a variety of intracellular and extracellular ubiquitous nucleolytic enzymes.

A number of chemical modifications have been introduced into antisense agents (i.e., oligonucleotides and oligonucleotide analogs) to increase their therapeutic activity. Such modifications are designed to increase cell penetration of the antisense agents, to stabilize the antisense agents from nucleases and other enzymes that degrade or interfere with their structure or activity in the body, to enhance the antisense agents binding to targeted RNA, to provide a mode of disruption (terminating event) once the antisense agents are sequence-specifically bound to targeted RNA, and to improve the antisense agents' pharmacokinetic and pharmacodynamic properties. It is unlikely that unmodified, "wild type," oligonucleotides will be useful therapeutic agents because they are rapidly degraded by nucleases.

Potential applications of these oligonucleotides and their modified derivatives as drugs have created new challenges in the large-scale synthesis of these compounds.

The solid phase synthesis of oligonucleotides is inherently wasteful in that more than one equivalent of nucleosidic phosphoramidite synthons is used presumably to drive the reaction to completion. Given the vast amounts of oligonucleotide syntheses performed for research use and for large scale manufacture pursuant to clinical trials, the waste of expensive nucleoside phosphoramidites is a significant economic and ecological problem. This problem becomes more acute if one has to synthesize the monomer through a multistep synthesis before reaching the phosphoramidite stage, as is the case where modified sugar or nucleobase containing synthons are used in oligonucleotide therapeutic agents.

Consequently, there remains a need in the art for synthetic methods which do not require the sacrifice of large amount of phosphoramidite reagent. The present invention addresses these, as well as other needs.

SUMMARY OF THE INVENTION

The present invention is directed to novel methods for the recovery of phosphoramidites from waste products of traditional phosphoramidite synthesis. In preferred embodiments, methods are provided for the preparation of phosphoramidites comprising the steps of:

reacting a compound of formula:

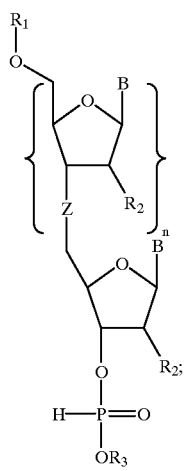

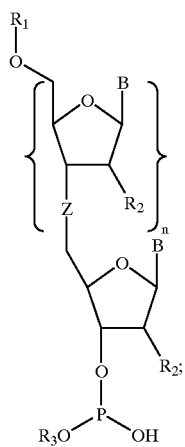

wherein:
Z is an internucleoside linkage;
$R_1$ is a hydroxyl protecting group;
$R_2$ is H, halogen, OH, O-alkyl, O-alkylamino, O-alkylalkoxy, a polyether of formula (O-alkyl)$_m$ where m is 1 to about 10, or a protected hydroxyl group;
$R_3$ is a phosphoryl protecting group;
B is a nucleobase; and
n is 0 to about 100;
with a compound of formula:

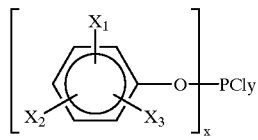

wherein:
$X_1$ is Br or Cl;
$X_2$ and $X_3$ are each, independently, H, Br or Cl;
x and y are each, independently, 2 or 3, and the sum of x and y is 5; and
contacting the product of the reaction with a compound of formula HN(Q)$_2$ to yield a phosphoramidite of formula:

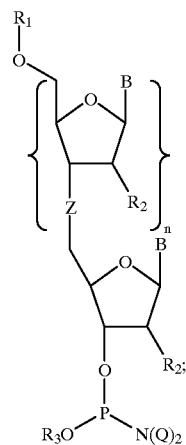

In some preferred embodiments Q is alkyl, preferably isopropyl.
$R_2$ is preferably H, a protected hydroxyl group, O-alkyl or O-alkylalkoxy. In more preferred embodiments $R_2$ is methoxyethoxy.
In some preferred embodiments $R_3$ is cyanoethyl, 4-cyano-2-butenyl, or diphenylmethylsilylethyl. Preferably, x is 3 and y is 2.
In prefered embodiments the reaction is performed in a solvent, which is preferably acetonitrile.
In some preferred embodiments the nucleobase is adenine, guanine, cytosine, thymine, uracil, 5-methyl cytosine or a protected derivative thereof.
In further preferred embodiments Z is a phosphodiester linkage, a phosphorothioate linkage, a phosphorodithioate linkage; or a phosphonate linkage. In particularly preferred embodiments Z is a phosphodiester linkage or a phosphorothioate linkage.

DETAILED DESCRIPTION OF PREFERRED EMBODIMENTS

The present invention presents novel methods for the preparation of phosphoramidites. The methods are useful for the recovery of a wide variety of species produced as waste products in oligonucleotide synthesis. In preferred embodiments, methods are provided for the preparation of phosphoramidites of formula:

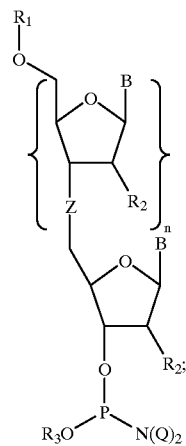

wherein Z is an internucleoside linkage; $R_1$ is a hydroxyl protecting group; $R_2$ is H, halogen, OH, O-alkyl, O-alkylamino, O-alkylalkoxy, a polyether of formula (O-alkyl)$_m$ where m is 1 to about 10, or a protected hydroxyl group; R$_3$ is a phosphoryl protecting group; B is a nucleobase; n is 0 to about 100, and each Q is independently alkyl having from 1 to 15 carbons, aryl having from 6 to 14 carbons, or (Q)$_2$ together with the phosphoamidite nitrogen can form a heterocyclic ring having from 2 to 10 carbons. The methods comprise the steps of reacting a compound of Formula I or II:

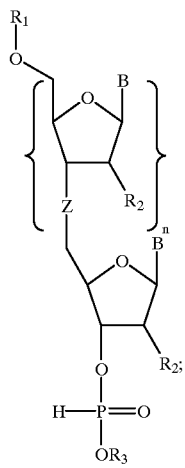

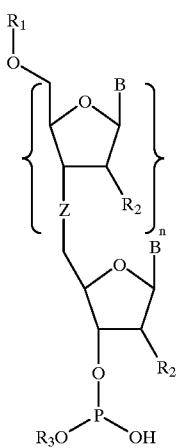

with a halophenoxychlorophosphorane of formula III:

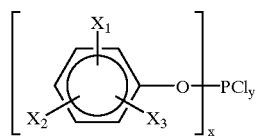

wherein:

X$_1$ is Br or Cl;

X$_2$ and X$_3$ are, independently, H, Br or Cl;

x and y are, independently, 2 or 3, with the sum of x and y being 5; and contacting the product of the reaction with a compound of formula HN(Q)$_2$.

Compounds of Formula I or II can derive from the waste excess phosphoramidite reagents used in traditional oligonucleotide synthesis, as described in, for example, *Oligonucleotides and Analogues: A Practical Approach*, Eckstein, F., Ed., IRL Press, Oxford, U. K. 1991, which is incorporated herein by reference in its entirety. In a typical oligonucleoide synthetic regime, the free 5-hydroxyl of the growing oligonucleotide chain is reacted with a several-fold molar excess of nucleoside N,N-dialkylphosphoramidite in the presence of excess tetrazole. It is believed that the tetrazole catalyst first displaces the secondary amino group of the phosphoramidite to form a tetrazolide addduct. The tetrazolide then reacts with the free 5'-hydroxyl of the growing chain to form a phosphite, which is subsequently transformed into the desired linkage by, for example, oxidation. The excess (i.e., unreacted) terazolide adduct is washed from the reaction chamber, and subsequently reacts with ambient water to form an H-phosphonate species represented by Formula I, which exists in equilibrium with its tautomer, represented by Formula II. Thus, in one aspect, the present invention provides a convenient method of recovering phosphoramidite synthons from waste products of oligonucleotide synthesis.

The methods of the present invention provide significant economic and ecological benefits in oligonucleotide synthesis. While not wishing to be bound by a particular theory, it is believed that the phosphonate species (Formula I) and its phosphite tautomer (Formula II) exist in equilibrium in solution, with the phosphonate species being heavily favored. The halophenoxychloro-phosphorane, preferably tris(2,4,6-tribromophenoxy) dichlorophosphorane or bis[2,4,6-tribromophenoxy] trichlorophosphorane, is believed to preferentially react with the phosphite species to form a halide adduct, which then reacts with a secondary amine to form the phosphoramidite product. Accordingly, the methods of the present invention can be conveniently perfomed in a single reaction container, or in stages.

The synthons of Formula I or II are derived from any of the wide variety of phosphoramidite species capable of being used in phosphoramidite ologomer synthesis. Accordingly, the synthons can be monomeric, dimeric, or higher order synthons (i.e., oligophosphoramidites), and can comprise any of the wide variety of internucleoside linkages, sugars, nucleobases, and modified derivatives thereof known in the art.

Examples of internucleoside linkages which can be present in synthons of Formula I or II include phosphodiester, phosphorothioate, phosphorodithioate, and phosphonate linkages. Further representative internucleotide linkages include amide or substituted amide linkages, such as those described in Waldner et al., *Synlett.* 1, 57–61 (1994), De Mesmaeker et al., *Synlett.* 10, 733–736 (1993), Lebreton et al., *Synlett.* 2, 137–140 (1994), De Mesmaeker et al., *Bioorg. Medic. Chem. Lett.* 4, 395–398 (1994), De Mesmaeker et al., *Bioorg. Medic. Chem. Lett.* 4, 873–878 (1994), Lebreton et al., *Tet. Letters* 34, 6383–6386 (1993), Lebreton et al., *Tet. Letters* 35, 5225–5228 (1994), Waldner et al., *Bioorg. Medic. Chem. Lett.* 4, 405–408 (1994), and linkgaes described in U.S. Pat. No. 5,489,677, U.S. Ser. No. 08/317,289, filed Oct. 3, 1994, U.S. Ser. No. 08/395,168, filed Feb. 27, 1995.

In the context of the present invention, the term "oligonucleotide" refers to a plurality of joined nucleotide units formed in a specific sequence. The term nucleotide has its accustomed meaning as the phosphoryl ester of a nucleoside. The term "nucleoside" also has its accustomed meaning as a pentofuranosyl sugar which is bound to a nucleosidic base (i.e, a nitrogenous heterocyclic base or "nucleobase").

It will be appreciated that the methods of the present invention can be used for the synthesis of phosphoramidites having both naturally occurring and non-naturally occurring constituent sugars, internucleoside linkages and/or nucleobases (i.e., nucleosidic bases). Non-naturally occurring sugars, internucleoside linkages and nucleobases are typically structurally distinguishable from, yet functionally interchangeable with, naturally occurring sugars (e.g. ribose and deoxyribose), internucleoside linkages (i.e. phosphodiester linkages), and nucleosidic bases (e.g., adenine, guanine, cytosine, thymine). Thus, non-naturally occurring moieties include all such structures which mimic the structure and/or function of naturally occurring moiety, and which aid in the binding of the oligonucleotide analog to a target, or otherwise advantageously contribute to the properties of the phosphorothioate oligomer.

Representative examples of non-naturally occurring sugars include sugars having any of a variety of substituents attached to their 2'-positions. These include, for example, halides, O-alkyl, O-alkylamino, O-alkylalkoxy, protected O-alkylamino, O-alkylaminoalkyl, O-alkyl imidazole, and polyethers of the formula (O-alkyl)$_m$, where m is 1 to about 10. Preferred among these polyethers are linear and cyclic polyethylene glycols (PEGs), and (PEG)-containing groups, such as crown ethers and those which are disclosed by Ouchi, et al., *Drug Design and Discovery* 1992, 9, 93, Ravasio, et al., *J Org. Chem.* 1991, 56, 4329, and Delgardo et. al., *Critical Reviews in Therapeutic Drug Carrier Systems* 1992, 9, 249. Further sugar modifications are disclosed in Cook, P. D., supra. Fluoro, O-alkyl, O-alkylamino, O-alkyl imidazole, O-alkylaminoalkyl, and alkyl amino substitution is described in U.S. Pat. application Ser. No. 08/398,901, filed Mar. 6, 1995, now U.S. Pat. No. 6,166,197, issued Dec. 26, 2000, entitled Oligomeric Compounds having Pyrimidine Nucleotide(s) with 2' and 5' Substitutions, the disclosure of which is hereby incorporated by reference.

Sugars having O-substitutions on the ribosyl ring are also amenable to the present invention. Representative substitutions for ring O include S, $CH_2$, CHF, and $CF_2$, see, e.g., Secrist, et al., Abstract 21, *Program & Abstracts, Tenth International Roundtable, Nucleosides, Nucleotides and their Biological Applications,* Park City, Utah, Sept. 16–20, 1992.

Representative nucleobases suitable for use in the methods of the invention include adenine, guanine, cytosine, uridine, and thymine, as well as other non-naturally occurring and natural nucleobases such as xanthine, hypoxanthine, 2-aminoadenie, 6-methyl and other alkyl derivatives of adenine and guanine, 2-propyl and other alkyl derivatives of adenine and guanine, 5-halo uracil and cytosine, 6-azo uracil, cytosine and thymine, 5-uracil (pseudo uracil), 4-thiouracil, 8-halo, oxa, amino, thiol, thioalkyl, hydroxyl and other 8-substituted adenines and guanines, 5-trifluoromethyl and other 5-substituted uracils and cytosines, 7-methylguanine. Further naturally and non naturally occurring nucleobases include those disclosed in U.S. Pat. No. 3,687,808 (Merigan, et al.), by Sanghvi, Y., in chapter 15 of *Antisense Research and Application,* Ed. S. T. Crooke and B. Lebleu, CRC Press, 1993, in Englisch et al., *Angewandte Chemie,* International Edition, 1991, 30, 613–722 (see especially pages 622 and 623), in the *Concise Encyclopedia of Polymer Science and Engineering,* J. I. Kroschwitz Ed., John Wiley & Sons, 1990, pages 858–859, and in Cook, P. D., *Anti-Cancer Drug Design,* 1991, 6, 585–607. The disclosures of each of the foregoing U.S. patents is incorporated by reference in their entirety. The terms "nucleosidic base" and "nucleobase" are further intended to include heterocyclic compounds that can serve as nucleosidic bases, including certain 'universal bases' that are not nucleosidic bases in the most classical sense, but function similarly to nucleoside bases. One representative example of such a universal base is 3-nitropyrrole.

The terms "nucleosidic base" and "nucleobase" are further intended to include heterocyclic compounds that can serve as nucleosidic bases, including certain 'universal bases' that are not nucleosidic bases in the most classical sense, but function similarly to nucleosidic bases. One representative example of such a universal base is 3-nitropyrrole.

In some preferred embodiments of the invention $R_1$ is a hydroxyl protecting group. A wide variety of hydroxyl protecting groups can be employed in the methods of the invention. Preferably, the protecting group is stable under basic conditions but can be removed under acidic conditions. Representative hydroxyl protecting groups are disclosed by Beaucage, et al., *Tetrahedron* 1992, 48, 2223–2311, and also in e.g., Green and Wuts, Protective Groups in Organic Synthesis, 2d edition, John Wiley & Sons, New York, 1991 at Chapter 2. Preferred protecting groups used for $R_1$ include dimethoxytrityl (DMT), monomethoxytrityl, 9-phenylxanthen-9-yl (Pixyl) and 9-(p-methoxyphenyl)xanthen-9-yl (Mox). The $R_1$ group can be removed from oligomeric compounds of the invention by techniques well known in the art to form the free hydroxyl. For example, dimethoxytrityl protecting groups can be removed by protic acids such as formic acid, dichloroacetic acid, trichloroacetic acid, p-toluene sulphonic acid or with Lewis acids such as for example zinc bromide.

In some preferred embodiments of the invention $R_3$ is a phosphoryl protecting group. The phosphoryl protecting group is attached to the phosphorus-bound oxygen, and serves to protect the phosphorus during oligonucleotide synthesis. See *Oligonucleotides and Analogues: A Practical Approach,* supra. One representative phosphoryl protecting group is the cyanoethyl group. Other representative phosphoryl protecting groups include 4-cyano-2-butenyl groups, methyl groups, and diphenylmethylsilylethyl (DPSE) groups.

In general, protecting groups are used in the oligonucleotide synthetic methods of the invention for protection of several different types of functionality. In general, protecting groups render chemical functionality inert to specific reaction conditions and can be appended to and removed from such functionality in a molecule without substantially damaging the remainder of the molecule. Representative protecting groups useful to protect nucleotides during phosphorothioate synthesis include base labile protecting groups and acid labile protecting groups. Base labile protecting groups are used to protect the exocyclic amino groups of the heterocyclic nucleobases. This type of protection is generally achieved by acylation. Two commonly used acylating groups are benzoylchloride and iso-butyrylchloride. These protecting groups are stable to the reaction conditions used in the methods of the invention, and during oligonucleotide synthesis, and are cleaved at approximately equal rates during the base treatment at the end of oligonuclotide synthesis. The second type of protection, also used in the synthetic methods of the invention, is an acid labile protecting group, which is used to protect the nucleotide 5'-hydroxyl during synthesis.

Tris[2,4,6-tribromophenoxy]dichlorophosphorane or bis [2,4,6-tribromophenoxy]trichlorophosphorane can be synthesized according to the method of Hotoda et al., Tetrahedron Letters 1987 28 (15) 1681–1684.

In the methods of the present invention, the product of the reaction between the compound of Formula I or II and the tribromophenoxychlorophosphorane reacts with a secondary amine to form the phosphoramidite product. The substituents of the secondary amine can be chosen from among the many species that are know to function as phosphoramidite nitrogen substituents. Representative examples include lower alkyl gourps, aryl groups, and cyclic structure such as where the phosphoramidite nitrogen forms part of a N-morpholine ring system. In particularly preferred embodiments the substituents are lower alkyl groups, especially isopropyl groups. Other examples of suitable amines as are described in various United States patents, principally those to M. Caruthers and associates. These include U.S. Pat. Nos. 4,668,777; 4,458,066; 4,415,732; and 4,500,707; all of which are herein incorporated by reference.

As used herein, the term "alkyl" includes but is not limited to straight chain, branch chain, and alicyclic hydrocarbon groups. Alkyl groups of the present invention may be substituted. Representative alkyl substituents are disclosed in U.S. Pat. No. 5,212,295, at column 12, lines 41–50.

As used herein, the term "aralkyl" denotes alkyl groups which bear aryl groups, for example, benzyl groups. The term "alkaryl" denotes aryl groups which bear alkyl groups, for example, methylphenyl groups. "Aryl" groups are aromatic cyclic compounds including but not limited to phenyl, naphthyl, anthracyl, phenanthryl, pyrenyl, and xylyl.

In some preferred embodiments of the invention amino groups are appended to alkyl or other groups, such as, for example, 2'-alkoxy groups (e.g., where $R_2$ is alkoxy). Such amino groups are also commonly present in naturally occurring and non-naturally occurring nucleobases. It is generally preferred that these amino groups be in protected form during the synthesis of oligomeric compounds of the invention. Representative amino protecting groups suitable for these purposes are discussed in Chapter 7 of Greene and Wuts, supra. Generally, as used herein, the term "nucleobase" includes protected derivatives thereof.

Oligomer phosphoramidites produced by the methods of the invention will preferably comprise from about 1 to about 100 monomer subunits. It is more preferred that such compounds comprise from about 1 to about 30 monomer subunits, with 1 to 10 monomer subunits being more preferred, and 1 to 5 monomer subunits being particularly preferred.

Additional advantages and novel features of this invention will become apparent to those skilled in the art upon examination of the examples thereof provided below, which should not be construed as limiting the appended claims.

EXAMPLE 1

Preparation of Tris(2,4,6-tribromophenoxy) dichlorophosphorane

This compound was synthesized according the procedure of Hotoda, H. et al., *Tetrahedron Letters*, 1987, Vol. 28, 1681–1684.

EXAMPLE 2

Preparation of 5'-O-(4,4'dimethoxytrityl)thymidine-3'-O-(2-diphenylmethylsilylethyl N,N-diisopropylphosphoramidite)

A 250 mL two necked flask equipped with a magnetic stirrer, a gas inlet for argon, and a septum is assembled under an argon atmosphere. All glassware are dried at 120° C. for 1 hour. The flask is charged with 5'-O-(4,4'dimethoxytrityl) thymidine-3'-O-(2-diphenylmethylsilylethylphosphonate) (0.015 mole) and diisopropylamine (0.12 mole). Anhydrous acetonitrile (200 mL) is added. To this stirred mixture under argon at room temperature is added tris(2,4,6-tribromophenoxy)dichlorophosphorane (0.225 mole). After stirring for three hours, the reaction mixture is filtered, and concentrated under reduced pressure. The crude product is purified by flash chromatography using silica gel to afford the desired product. Triethylamine (1%) is used throughout the purification. $^{31}$P NMR (CDCl$_3$) 145.5, 146.1

EXAMPLE 3

Preparation of $N^2$-Isobutyryl-5'-O-(4,4'dimethoxytrityl)-2'-deoxyguanosine-3'-O-(2-diphenylmethylsilylethyl N,N-diisopropylphosphoramidite)

A 250 mL two necked flask equipped with a magnetic stirrer, a gas inlet for argon, and a septum is assembled under an argon atmosphere. All glassware are dried at 120° C. for 1 hour. The flask is charged with $N^2$-Isobutyryl-5'-O-(4,4'-dimethoxytrityl)-2'-deoxyguanosine-3'-O-(2-diphenylmethylsilylethylphosphonate) (0.015 mole) and diisopropylamine (0.12 mole). Anhydrous acetonitrile (200 mL) is added. To this stirred mixture under argon at room temperature is added tris(2,4,6-tribromophenoxy) dichlorophosphorane (0.225 mole). After stirring for three hours, the reaction mixture is filtered, and concentrated under reduced pressure. The crude product is purified by flash chromatography using silica gel to afford the desired product. Triethylamine (1%) is used throughout the purification.

EXAMPLE 4

Preparation of $N^6$-Benzoyl-5'-O-(4,4'dimethoxytrityl)-2'-deoxyadenosine-3'-O-(2-diphenylmethylsilylethyl N,N-diisopropylphosphoramidite)

A 250 mL two necked flask equipped with a magnetic stirrer, a gas inlet for argon, and a septum is assembled under an argon atmosphere. All glassware are dried at 120° C. for 1 hour. The flask is charged with $N^6$-Benzoyl-5'-O-(4,4'-dimethoxytrityl)-2'-deoxyadenosine- 3'-O-(2-diphenylmethylsilylethylphosphonate) (0.015 mole) and diisopropylamine (0.12 mole). Anhydrous acetonitrile (200 mL) is added. To this stirred mixture under argon at room temperature is added tris(2,4,6-tribromophenoxy) dichlorophosphorane (0.225 mole). After stirring for three hours, the reaction mixture is filtered, and concentrated under reduced pressure. The crude product is purified by flash chromatography using silica gel to afford the desired product. Triethylamine (1%) is used throughout the purification.

EXAMPLE 5

Preparation of $N^4$-Benzoyl-5'-O-(4,4'dimethoxytrityl)-2'-deoxycytidine-3'-O-(2-diphenylmethylsilylethyl N,N-diisopropylphosphoramidite)

A 250 mL two necked flask equipped with a magnetic stirrer, a gas inlet for argon, and a septum is assembled under an argon atmosphere. All glassware are dried at 120° C. for 1 hour. The flask is charged with $N^4$-Benzoyl-5'-O-(4,4,'dimethoxytrityl)-2'-deoxycytidine-3'-O-(2-diphenylmethylsilylethylphosphonate) (0.015 mole) and diisopropylamine (0.12 mole). Anhydrous acetonitrile (200 mL) is added. To this stirred mixture under argon at room temperature is added tris(2,4,6-tribromophenoxy) dichlorophosphorane (0.225 mole). After stirring for three hours, the reaction mixture is filtered, and concentrated under reduced pressure. The crude product is purified by flash chromatography using silica gel to afford the desired product. Triethylamine (1%) is used throughout the purification.

EXAMPLE 6

2-Diphenylmethylsilylethyl-5'-(O-4,4'-dimethoxytrityl)-thymidinyl-thymidine dimer amidite A 250 mL two necked flask equipped with a magnetic stirrer, a gas inlet for argon, and a septum is assembled under an argon atmosphere. All glassware are dried at 120° C. for 1 hour. The flask is charged with 2-diphenylmethyl-silylethyl-5'-(O-4,4'-dimethoxytrityl)-thymidinyl-thyidine dimer phosphonate (0.015 mole) and diisopropylamine (0.12 mole). Anhydrous acetonitrile (200 mL) is added. To this stirred mixture under argon at room temperature is added tris(2,4,6-tribromophenoxy)dichlorophosphorane (0.225 mole). After stirring for three hours, the reaction mixture is filtered, and concentrated under reduced pressure. The crude product is purified by flash chromatography using silica gel to afford the desired product. Triethylamine (1%) is used throughout the purification.

EXAMPLE 7

2-Diphenylmethylsilylethyl-5'-(O-4,4'-dimethoxytrityl)-N$^4$-benzoyl-2'-deoxycytidinyl-thymidine dimer amidite A 250 mL two necked flask equipped with a magnetic stirrer, a gas inlet for argon, and a septum is assembled under an argon atmosphere. All glassware are dried at 120° C. for 1 hour. The flask is charged with 2-diphenylmethyl-silylethyl-5'-(O-4,4'-dimethoxytrityl)-N$^4$-benzoyl-2'-deoxycytidinyl-thymidine dimer phosphonate (0.015 mole) and diisopropylamine (0.12 mole). Anhydrous acetonitrile (200 mL) is added. To this stirred mixture under argon at room temperature is added tris(2,4,6-tribromophenoxy) dichlorophosphorane (0.225 mole). After stirring for three hours, the reaction mixture is filtered, and concentrated under reduced pressure. The crude product is purified by flash chromatography using silica gel to afford the desired product. Triethylamine (1%) is used throughout the purification.

EXAMPLE 8

2-Diphenylmethylsilylethyl-5'-(O-4,4'-dimethoxytrityl)-N$^2$-isobutyryl-2'-deoxyguanosinyl-thymidine dimer amidite A 250 mL two necked flask equipped with a magnetic stirrer, a gas inlet for argon, and a septum is assembled under an argon atmosphere. All glassware are dried at 120° C. for 1 hour. The flask is charged with 2-diphenylmethyl-silylethyl-5'-(O-4,4'-dimethoxytrityl)-N$^2$-isobutyryl-2'-deoxyguanosinyl-thymidine dimer phosphonate (0.015 mole) and diisopropylamine (0.12 mole). Anhydrous acetonitrile (200 mL) is added. To this stirred mixture under argon at room temperature is added tris(2,4,6-tribromophenoxy) dichlorophosphorane (0.225 mole). After stirring for three hours, the reaction mixture is filtered, and concentrated under reduced pressure. The crude product is purified by flash chromatography using silica gel to afford the desired product. Triethylamine (1%) is used throughout the purification.

EXAMPLE 9

2-Diphenylmethylsilylethyl-5'-(O-4,4'-dimethoxytrityl)-N$^6$-benzoyl-2'-deoxyadenosinyl-thymidine diner amidite A 250 mL two necked flask equipped with a magnetic stirrer, a gas inlet for argon, and a septum is assembled under an argon atmosphere. All glassware are dried at 120° C. for 1 hour. The flask is charged with 2-diphenylmethyl-silylethyl-5'-(O-4,4'-dimethoxytrityl)-N$^6$-benzoyl-2'-deoxyadenosinyl-thymidine dimer phosphonate (0.015 mole) and diisopropylamine (0.12 mole). Anhydrous acetonitrile (200 mL) is added. To this stirred mixture under argon at room temperature is added tris(2,4,6-tribromophenoxy) dichlorophosphorane (0.225 mole). After stirring for three hours, the reaction mixture is filtered, and concentrated under reduced pressure. The crude product is purified by flash chromatography using silica gel to afford the desired product. Triethylamine (1%) is used throughout the purification.

EXAMPLE 10

2-Diphenylmethylsilylethyl-5'-(O-4,4'-dimethoxytrityl)-N$^2$-isobutyryl-2'-deoxyguanosinyl-N6-benzoyl-2'-deoxyadenosinyl dimer amidite A 250 mL two necked flask equipped with a magnetic stirrer, a gas inlet for argon, and a septum is assembled under an argon atmosphere. All glassware are dried at 120° C. for 1 hour. The flask is charged with 2-diphenylmethyl-silylethyl-5'-(O-4,4'-dimethoxytrityl)-N$^2$-isobutyryl-2'-deoxyguanosinyl-N6-benzoyl-2'-deoxyadenosinyl dimer phosphonate (0.015 mole) and diisopropylamine (0.12 mole). Anhydrous acetonitrile (200 mL) is added. To this stirred mixture under argon at room temperature is added tris(2,4,6-tribromophenoxy)dichlorophosphorane (0.225 mole). After stirring for three hours, the reaction mixture is filtered, and concentrated under reduced pressure. The crude product is purified by flash chromatography using silica gel to afford the desired product. Triethylamine (1%) is used throughout the purification.

EXAMPLE 11

Preparation of 5'-O-(4,4'dimethoxytrityl)uridine-2'-O-methoxyethyl-3'-O-(2-diphenylmethylsilylethyl N,N-diisopropylphosphoramidite)

A 250 mL two necked flask equipped with a magnetic stirrer, a gas inlet for argon, and a septum is assembled under an argon atmosphere. All glassware are dried at 120° C. for 1 hour. The flask is charged with 5'-O-(4,4'dimethoxytrityl) uridine-2'-O-methoxyethyl-3'-O-(2-diphenylmethylsilyl-ethylphosphonate) (0.015 mole) and diisopropylamine (0.12 mole). Anhydrous acetonitrile (200 mL) is added. To this stirred mixture under argon at room temperature is added tris(2,4,6-tribromophenoxy)dichlorophosphorane (0.225 mole). After stirring for three hours, the reaction mixture is filtered, and concentrated under reduced pressure. The crude product is purified by flash chromatography using silica gel to afford the desired product. Triethylamine (1%) is used throughout the purification. $^{31}$P NMR (CDCl$_3$) 145.5, 146.1

EXAMPLE 12

Preparation of $N^2$-Isobutyryl-5'-O-(4, 4'dimethoxytrityl)-2'-O-methoxyethylguanosine-3'-O-(2-diphenylmethylsilylethyl N,N-diisopropylphosphoramidite)

A 250 mL two necked flask equipped with a magnetic stirrer, a gas inlet for argon, and a septum is assembled under an argon atmosphere. All glassware are dried at 120° C. for 1 hour. The flask is charged with $N^2$-Isobutyryl-5'-O-(4, 4'dimethoxytrityl)-2'-O-methoxyeth ylguanosine-3'-O-(2-diphenylmethylsilylethylphosphonate) (0.015 mole) and diisopropylamine (0.12 mole). Anhydrous acetonitrile (200 ML) is added. To this stirred mixture under argon at room temperature is added tris(2,4,6-tribromophenoxy) dichlorophosphorane (0.225 mole). After stirring for three hours, the reaction mixture is filtered, and concentrated under reduced pressure. The crude product is purified by flash chromatography using silica gel to afford the desired product. Triethylamine (1%) is used throughout the purification.

EXAMPLE 13

Preparation of $N^6$-Benzoyl-5'-O-(4, 4'dimethoxytrityl)-2'-O-methoxyethyladenosine-3'-O-(2-diphenylmethylsilylethyl N,N-diisopropylphosphoramidite)

A 250 mL two necked flask equipped with a magnetic stirrer, a gas inlet for argon, and a septum is assembled under an argon atmosphere. All glassware are dried at 120° C. for 1 hour. The flask is charged with $N^6$-Benzoyl-5'-O-(4, 4'dimethoxytrityl)-2'-O-methoxyethyla denosine-3'-O-(2-diphenylmethylsilylethylphosphonate) (0.015 mole) and diisopropylamine (0.12 mole). Anhydrous acetonitrile (200 mL) is added. To this stirred mixture under argon at room temperature is added tris(2,4,6-tribromophenoxy) dichlorophosphorane (0.225 mole). After stirring for three hours, the reaction mixture is filtered, and concentrated under reduced pressure. The crude product is purified by flash chromatography using silica gel to afford the desired product. Triethylamine (1%) is used throughout the purification.

EXAMPLE 14

Preparation of $N^4$-Benzoyl-5'-O-(4,4, dimethoxytrityl)-2'-O-methoxyethylcytidine-3'-O-(2-diphenylmethylsilylethyl N,N-diisopropylphosphoramidite)

A 250 mL two necked flask equipped with a magnetic stirrer, a gas inlet for argon, and a septum is assembled under an argon atmosphere. All glassware are dried at 120° C. for 1 hour. The flask is charged with $N^4$-Benzoyl-5'-O-(4, 4'dimethoxytrityl)-2'-O-methoxyethylcytidine-3'-O-(2-diphenylmethylsilylethylphosphonate) (0.015 mole) and diisopropylamine (0.12 mole). Anhydrous acetonitrile (200 mL) is added. To this stirred mixture under argon at room temperature is added tris(2,4,6-tribromophenoxy) dichlorophosphorane (0.225 mole). After stirring for three hours, the reaction mixture is filtered, and concentrated under reduced pressure. The crude product is purified by flash chromatography using silica gel to afford the desired product. Triethylamine (1%) is used throughout the purification.

It is intended that each of the patents mentioned or referred to in this specification be herein incorporated by reference in their entirety.

As those skilled in the art will appreciate, numerous changes and modifications may be made to the preferred embodiments of the invention without departing from the spirit of the invention. It is intended that all such variations fall within the scope of the invention.

What is claimed is:

1. A compound of formula:

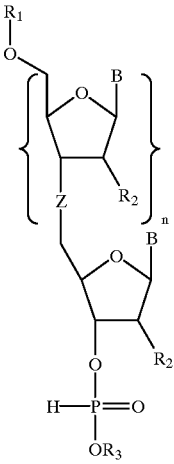

wherein:

Z is an intersugar linkage;

$R_1$ is a hydroxyl protecting group;

$R_2$ is H, OH, O-alkyl, O-alkylamino, O-alkylalkoxy, a polyether of formula $(O\text{-alkyl})_m$ where m is 1 to about 10, or a protected hydroxyl group;

$R_3$ is 4-cyano-2-butenyl or diphenylmethylsilylethyl;

B is a nucleobase; and n is 1 to about 100.

2. The compound of claim 1 wherein $R_2$ is H.

3. The compound of claim 1 wherein $R_2$ is a protected hydroxyl group.

4. The compound of claim 1 wherein $R_2$ is O-alkyl or O-alkylalkoxy.

5. The compound of claim 1 wherein $R_2$ is O-alkylalkoxy.

6. The compound of claim 1 wherein $R_2$ is methoxyethoxy.

7. The compound of claim 1 wherein the nucleobase is 9-adeninyl, 9-guaninyl, 1-cytosinyl, 1-thyminyl, 1-uracilyl, 5-methyl-1-cytosinyl or a protected derivative thereof.

8. The compound of claim 1 wherein Z is a phosphodiester linkage, a phosphorothioate linkage, a phosphorodithioate linkage; or a phosphonate linkage.

9. The compound of claim 8 wherein Z is a phosphodiester linkage or a phosphorothioate linkage.

10. The compound of claim 1 wherein $R_3$ is cyanoethyl.

11. The compound of claim 1 wherein $R_3$ is 4-cyano-2-butenyl.

12. The compound of claim 1 wherein $R_3$ is 4-cyano-2-butenyl or diphenylmethylsilylethyl; B is 9-adeninyl, 9-guaninyl 1-cytosinyl, 1-thyminyl, 1-uracilyl 5-methyl-1-cytosinyl or a protected derivative thereof; and Z is a phosphodiester linkage or a phosphorothioate linkage.

13. A compound of formula:

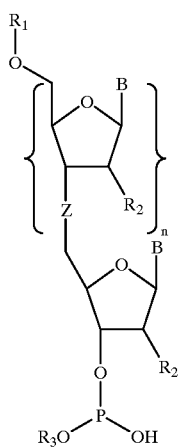

wherein:
- Z is an intersugar linkage;
- $R_1$ is a hydroxyl protecting group;
- $R_2$ is H, OH, O-alkyl, O-alkylamino, O-alkylalkoxy, a polyether of formula $(O\text{-alkyl})_m$ where m is 1 to about 10, or a protected hydroxyl group;
- $R_3$ is 4-cyano-2-butenyl or diphenylmethylsilylethyl;
- B is a nucleobase; and
- n is 1 to about 100.

14. The compound of claim 13 wherein $R_2$ is H.

15. The compound of claim 13 wherein $R_2$ is a protected hydroxyl group.

16. The compound of claim 13 wherein $R_2$ is O-alkyl or O-alkylalkoxy.

17. The compound of claim 13 wherein $R_2$ is O-alkylalkoxy.

18. The compound of claim 13 wherein $R_2$ is methoxyethoxy.

19. The compound of claim 13 wherein the nucleobase is 9-adeninyl, 9-guaninyl, 1-cytosinyl, 1-thyminyl, 1-uracilyl, 5-methyl-1-cytosinyl or a protected derivative thereof.

20. The compound of claim 13 wherein Z is a phosphodiester linkage, a phosphorothioate linkage, a phosphorodithioate linkage; or a phosphonate linkage.

21. The compound of claim 20 wherein Z is a phosphodiester linkage or a phosphorothioate linkage.

22. The compound of claim wherein $R_3$ is cyanoethyl.

23. The compound of claim 13 wherein $R_3$ is 4-cyano-2-butenyl.

24. The compound of claim 13 wherein $R_3$ is 4-cyano-2-butenyl, or diphenylmethylsilylethyl; B is 9-adeninyl, 9-guaninyl, 1-cytosinyl, 1-thyminyl, 1-uracilyl, 5-methyl-1-cytosinyl or a protected derivative thereof; and Z is a phosphodiester linkage or a phosphorothioate linkage.

* * * * *